United States Patent [19]

Nakanishi et al.

[11] Patent Number: 4,773,904
[45] Date of Patent: Sep. 27, 1988

[54] ABSORBENT ARTICLE

[75] Inventors: Minoru Nakanishi; Akira Sakurai, both of Utsunomiya, Japan

[73] Assignee: Kao Corporation, Tokyo, Japan

[21] Appl. No.: 906,206

[22] Filed: Sep. 12, 1986

[30] Foreign Application Priority Data

Sep. 18, 1985 [JP] Japan .................................. 60-205900

[51] Int. Cl.$^4$ .............................................. A61F 13/16
[52] U.S. Cl. ...................................... 604/372; 604/374; 604/375; 604/378; 428/286; 428/343; 428/507; 428/522; 428/537.1; 428/537.5
[58] Field of Search ............... 428/343, 286, 507, 522, 428/537.1, 537.5; 604/372, 374, 375, 378, 385.1

[56] References Cited

U.S. PATENT DOCUMENTS

| | | | |
|---|---|---|---|
| 4,219,024 | 8/1980 | Karami | 604/372 |
| 4,323,069 | 4/1982 | Ahr et al. | 604/372 |
| 4,622,036 | 11/1986 | Goodrum | 604/372 |
| 4,626,252 | 12/1986 | Nishizawa et al. | 604/372 |

*Primary Examiner*—Edith Buffalow
*Attorney, Agent, or Firm*—Birch, Stewart, Kolasch & Birch

[57] ABSTRACT

An absorbent article comprises a surface sheet, an absorbent and a back sheet, a part or all, being not to contact the skin, of said back sheet having the below listed three requirements:
(a) a coefficient of a kinetic friction against an acrylic resin plate is 1.5 or higher,
(b) it is elastic so that it breaks at a length of 300 or larger percent based on the original length, and
(c) a force to stretch it by 50 percent based on the original length is 100 kg/cm2 or larger.

6 Claims, 2 Drawing Sheets

FIG. 1(a)
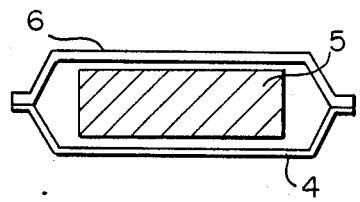
FIG. 1(e)
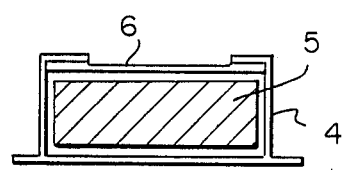
FIG. 1(b)
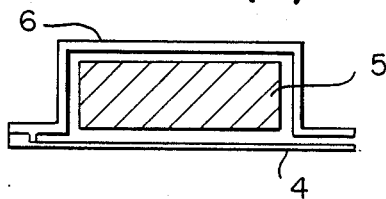
FIG. 1(f)
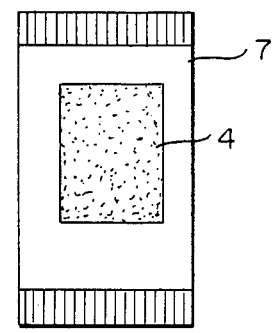
FIG. 1(c)
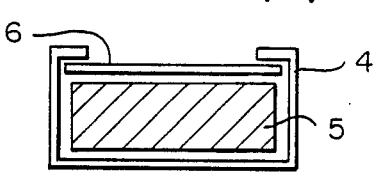
FIG. 1(g)
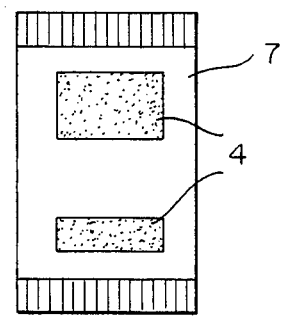
FIG. 1(d)
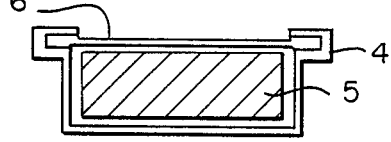
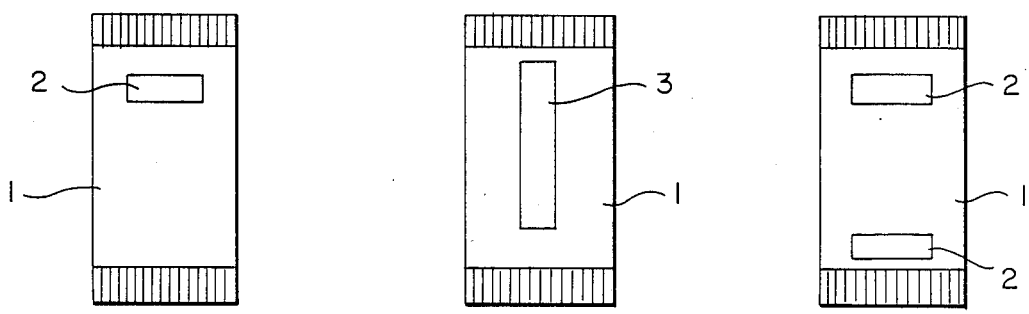
FIG. 2(a)   FIG. 2(b)   FIG. 2(c)

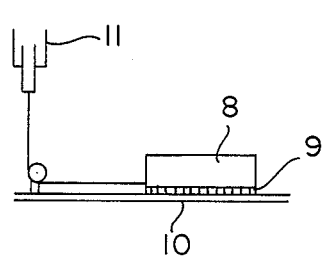
FIG. 3
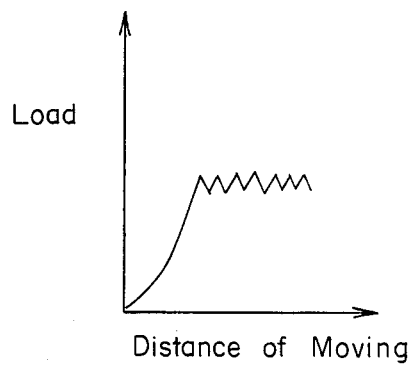
FIG. 4
FIG. 5
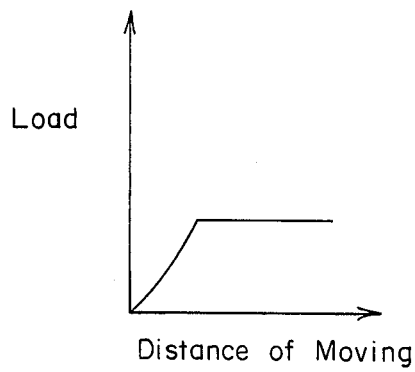
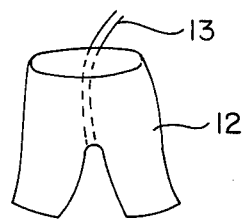
FIG. 6
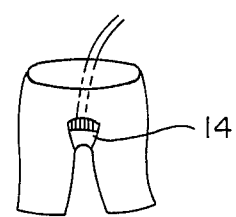
FIG. 7

ABSORBENT ARTICLE

The present invention relates to an absorbent article such as a sanitary napkin, a pad for an incontinent person, or a pad for hemorrhoids, and specifically to an absorbent article having anti-slipperiness and an elasticity providing a capacity of following the movement of the wearing part of a body in at least part of the surface of the article out of contact with the skin.

STATEMENT OF PRIOR ARTS

A conventional absorbent article such as a sanitary napkin, a pad for an incontinent person, or a pad for hemorrhoids comprises an absorbent layer made of pulp, absorbent paper, or the like; a leak-proof sheet generally called "poly-lami, water-proof paper" having a water-proof paper, a polyethylene film, or the like laminated thereon for the purpose of leak prevention; and a surface material covering the surfaces and outer sides of the article.

Performance characteristics required of such an absorbent article are high absorption rate and high retentivity. For these purposes, various improvements of the surface material, using a superabsorbent polymer, have been made. For example, see Japanese patent publications A (unexamined) Nos. 55,260/78 and 107,191/79 Those prior arts do not meet the above shown purposes satisfactorily.

No matter how the performance of the absorbent layer may be improved, however, much mill be detracted from this imrovement, when a fit to the crotch is poor or when the displacement, such as slippage, of the absorbent article from a regular position occurs due to the movement of the user during the use of the article. For example, an anti-slippage tape of a sanitary napkin was provided for the first time over ten years ago and has been employed up to now. The sanitary napkin will be taken as a representative example of the absorbent article, and will be described hereinbelow.

During these years, a double-sided, pressure-sensitive adhesive tape and a hot-melt tape have been provided as a material for the anti-slippage tape and, structurally, a pressure-sensitive adhesive tape of about 10 to 15 mm in length and about 40 to 50 mm in width or a hot-melt tape of 160 to 190 mm in length and 3 to 5 mm in width applied to an absorbent article by sticking or coating and covered with a release paper has been mainly provided.

With these conventional anti-slippage tapes, however, difficulty has been experienced in determining a proper position for placing the sanitary napkin, resulting in poor fit and feelings of discomfort. Besides, since motion during walking or exercise is fundamentally different between the front and buttock sides of a crotch, slippage or displacement of the sanitary napkin itself occurs, resulting in such an insufficient effect as to sometimes cause leak in absorption of menstrual blood. This is, needless to say, fundamentally detrimental to the performance of the absorbent article, and gives mental uneasiness to the users.

BRIEF DESCRIPTION OF THE DRAWINGS

FIG. 1a–g includes crosssectional and plan views of various examples of the absorbent article of the present invention.

FIG. 2 includes plan views of examples of conventional absorbent articles having a slippage preventing tape(s) disposed on the surface thereof out of contact with the skin.

FIG. 3 is a schematic crosssectional view of a kinetic friction coefficient measuring apparatus.

FIG. 4 is a chart of the article of the present invention in translational motion in a Tensilon tensile tester.

FIG. 5 is a chart of the comparative article in translational motion in the Tensilon tensile tester.

FIG. 6 is a perspective view of a movable female waist model.

FIG. 7 is a perspective view showing a state of a test piece being set on the model as shown in FIG. 6.

1: conventional absorbent article, 2: double-sided pressure-sensitive adhesive tape, 3: hot-melt adhesive, 4: elastomer sheet, 5: absorbent material, 6: surface material, 7: surface out of contact with skin, 8: weight, 9: elastomer sample, 10: smooth acrylic plate, 11: chuck of Tensilon tensile tester, 12: body of movable female waist model, 13: liquid injection tube, 14: test piece.

The problems involved in the anti-slippage tapes of conventional absorbent articles will now be described in detail with reference to the attached drawings. FIG. 2 shows various forms of anti-slippage tapes mounted on the non-effective surfaces (surfaces out of contact with the skin) of conventional absorbent articles.

Among them, the one as shown in FIG. 2(a) is very common. A double-sided pressure-sensitive adhesive tape 2 is laterally provided in one portion of the front of an absorbent article 1. This type of the tape which is called "lateral one-portion tape" accounts for most of commercially available anti-slippage tapes. It involves a relatively small problem of easiness in wearing as compared with others, but has a defect in that it provides for only a small anti-slippage effect which is an essential purpose, and particularly a small effect of preventing lateral slippage on the buttock side (the side carrying no anti-slippage tape).

On the other hand, FIG. 2(b) applies mainly to a case where a hot-melt type is employed. A hot-melt adhesive 3 is provided longitudinally on an absorbent article 1. This type of the tape is called "longitudinal tape." It may be regarded as improved in lateral slippage preventing ability in comparison with the former type, but does not actually provide such an effect and, on the contrary, causes slippage or a feeling of discomfort in many cases. This is believed to be because the central portion of the anti-slippage tape is bent in the crotch when putting on the napkin and assumes a peculiar form in the lateral direction as the case may be, and the form is then fixed. Therefore, the effective contact area of the tape with shorts drastically decreases, leading to the above-mentioned defects.

The form as shown in FIG. 2(c) may be regarded as the one proposed mainly with a view to improving the lateral slippage preventing ability. Double-sided, pressure-sensitive adhesive tapes 2 are provided on an absorbent article 1 in respective two portions in the front and rear thereof. This "lateral two-portion tape" also involves basically the same defects as in the above-mentioned longitudinal tape. Specifically, since the tape is bonded to shorts with a form fixed in the longitudinal direction on putting on the napkin, a difference arises between the fixed form and a form to be assumed in the subsequent usual service state. Thus, wearing, with consideration being given to that point is difficult or, even if possible, will be troublesome whatever efforts may be made.

Anti-slippage materials having a portion where a fiber of nylon, rayon, or the like is bristled have been proposed in Japanese utility model publications A (unexamined) Nos. 44,097/75, 44,098/75 and 44,099/75. Those disclosed materials, however, have a defect that a difficulty is encountered in setting them in a proper position on putting on the napkin, so that they may be set in a state different from a complicated form of a crotch, leading to side leak during walking or exercise.

For the same purpose, methods of using a structure having a relatively high friction coefficient in the contacting surface thereof, such as a foamed structure made of a foamed urethane or a bristled structure made of a flocked fabric have been proposed as non-pressure-sensitive adhesive type of anti-slippage materials, in Japanese utility model publications A (unexamined) Nos. 46,319/83, 105,318/83 and 33,412/84. However, the anti-slip effect of the coarsened surface material such as a foamed structure is not so large. Thus, no sufficient slippage preventing effect in the actual service can be expected with only such a structure. In view of this, methods of combined use of such a structure with a pressure-sensitive adhesive material have been proposed. For example see Japanese unitlity model publications A (unexamined) Nos. 88,421/84 and 73,522/85. In those methods, rubber-like properties of a foamed material are utilized mainly with a view to improving the fit to a surface to be in contact therewith.

In the case of a flocked fabric, since it has a friction coefficient higher than that of a foamed material, a sufficient anti-slippage effect can be expected. However, since the flocked fabric itself has poor stretchability, the fit in a wearing position is poor and difficulty is essentially encountered in making the speed in the bristling step follow the normal speed of napkin fabricaiton, disadvantageously leading to a decrease in the fabrication speed.

Both of the above-mentioned structures necessitate an adhesive or the like in effecting integration thereof with a napkin or the like. This does not favorably affect the processing and the cost.

SUMMARY OF THE INVENTION

As a result of intensive investigations with a view to solving these problems, the present inventors have completed the present invention.

An object of the present invention is to provide an absorbent article having an anti-slippage material which facilitates the determination of a position where the article is put on during its use, and which exhibits effective slippage preventing ability against various movements of a crotch during the use of the article.

The present invention, which has been accomplished with a view to attaining such an object and providing an absorbent article beneficial to the users, specifically relates to an absorbent article having an anti-slippage material which does not require so high a technical level in the manufacture, which facilitates the determination of a position where the article is put on in its use, and which exhibits an effective slippage preventing ability against various movements of a crotch during the use of the article.

An absorbent article of the invention comprises a surface sheet, an absorbent and a back sheet, a part or all of said back sheet not in contact with, the skin, said back sheet having the following three requirements:

(a) a coefficient of kinetic friction against an acrylic resin plate of 1.5 or higher, (b) said back sheet being elastic so that it breaks at a length of 300 percent or greater based on the original length, and (c) a force of 100 kg/cm$^2$ or less to stretch said back sheet by 50 percent based on the original length.

In way of material, a part or all of said back sheet having the above listed requirements is preferably formed from an elastomer such as a conjugated diene polymer, polyethylene, polypropylene, polybutylene and polyvinylidene chloride.

Specifically, the present invention provides an absorbent article characterized in that at least part of a surface constituting the surface thereof out of contact with the skin satisfies the following requirements (a) to (c):

(a) a coefficient of kinetic friction with regard to an acrylic plate of 1.5 or higher, (b) such an elasticity as to provide a length in breaking of 300% or more based on the original length, and (c) a force for stretching by 50% based on the original length of 100 kg/cm$^2$ or less.

The material satisfying the above-mentioned requirements (a) to (c) which can be used in the absorbent article of the present invention for constituting at least part of a surface out of contact with the skin may be an elastomer sheet or film formed by customary molding (T die, inflation, or the like) or expansion molding of a resin derived from a conjugated diene such as butadiene or a lower alkene such as ethylene or butylene. Among others, the foamed type includes, for example, a product commercially available under the trade name of Kalsoft (foamed polybutadiene manufactured by Takiron Co., Ltd.).

However, the material is not limited to those mentioned above, and a resin used in a stretch film for foodstuff packaging (for example, polyvinylidene chloride) can also be essentially used.

Such an elastomer, due to a high stretchability and a low rubber modulus (tensile stress in 50% elongation), elongates in the direction of slippage stress before movement of slippage when slippage stress is caused on the contacting surface, and continues to elongate by itself in a state of contact of the elastomer with the contacting surface. When the elongation of the elastomer sheet progresses to such an extent that the tensile stress exceeds the slippage resistance, the sheet gives rise to a slippage movement, in the course of which the sheet is shrunken because it undergoes stress relaxation due to translational motion thereof, whereupon the translational motion of the sheet stops, followed by elongation of the sheet again. In this way, the elastomer undergoes a process of elongation-shrinkage.

As described above, since the elastomer moves like a measuring worm in accordance with slippage stress, a high slippage resistance is produced so that slippage can be effectively prevented.

The elastomer is preferably thermoplastic since it can be advantageously integrated with, for example, a napkin by heat sealing. Needless to say, however, this is not an essential requirement.

An embodiment of the absorbent article of the present invention will now be described with reference to the accompanying drawings, in which:

FIG. 1 includes crosssectional and plan views of various examples of the absorbent article of the present invention with an elastomer sheet 4, an absorbent material 5, a surface material 6, and a surface 7 out of contact with the skin. Among them, (a) to (e) are each of a type of an anti-slippage material also serving as the leak-proof material, and (c) is of a wound-up type while (d) is of a folded type.

Besides the above-mentioned mode of using an anti-slippage sheet all over the surface out of contact with the skin, a mode of using an anti-slippage sheet in the form of a tape like the conventional mode as in (f) and (g), namely using it in only part of the surface 7 out of contact with the skin, can exert a sufficient slippage preventing effect as well. In this case, the elastomer 4 preferably occupies 20% or more of the surface 7 out of contact with the skin. The mode of using an anti-slippage sheet all over the surface out of contact with the skin is preferred since the customary leak-proof material can be dispensed with and the slippage preventing effect is greater.

Since the absorbent article of the present invention has a highly stretchable, flexible elastomer having a high slippage resistance and disposed in the lowermost layer (surface out of contact with the skin), an effective contact with shorts or the like can be secured in a worn state to effectively prevent slippage with the high friction resistance. Since this slippage preventing action is non-adhesive unlike the conventional modes, there arises no disadvantage that, when the article unfortunately is not worn in a normal form as it should be, a difficulty is encountered in reverting it to the normal form owing to mutual adhesive bonding. Thus, once the article is fit to the form of a crotch, the above-mentioned slippage preventing effect is exerted.

Further, since the elastomer is highly stretchable and flexible, the revertibility is good even when it is deformed by movement in a worn state, so that it can easily adapt itself to movement of the body without wrinkling or flattening. This promotes together with the slippage preventing effect a leak-proof effect.

[EXAMPLES]

The following Examples will illustrate the present invention in more detail.

Example 1

The physical properties of three kinds of representative materials that may be used as the elastomer in the present invention are listed in Table 1.

The breaking strength is a stress in breaking, while the breaking elongation is a percentage of elongation in a given direction when the material is broken, namely {(elongated size in breaking-usual size)÷usual size}×100. 50% rubber modulus is a value of stress in 50% elongation.

Example 2

The measurement of a coefficient of kinetic friction, which indicates the slippage preventing ability, was made as to the elastomer materials 1 to 3 as used in Example 1 according to the present invention. The coefficient of kinetic friction was measured by using an apparatus as shown in FIG. 3. Specifically, a weight 8 was placed on an elastomer sample 9 on a smooth acrylic plate 10, and the measurement was conducted by pulling the weight of 240 g horizontally at a pulling speed of 100 mm/min in a Tensilon tensile tester. In FIG. 3, numeral 11 indicates a chuck of a tensile strength tester.

The measurement of the coefficient of kinetic friction was also made as to a foamed urethane and polyethylene (LDPE) as controls.

The results are shown in Table 2.

TABLE 2

| Test piece | Tensile load in movement (g) | Coefficient of kinetic friction |
|---|---|---|
| Sample 1 according to the present invention | 560 | 2.33 |
| Sample 2 according to the present invention | 475 | 1.98 |
| Sample 3 according to the present invention | 486 | 2.03 |
| Comparative sample 1 (foamed urethane) | 200 | 0.83 |
| Comparative sample 2 polyethylene (LDPE) | 293 | 1.22 |

It will be understood from Table 2 that the elastomer materials according to the present invention show a coefficient of kinetic friction of as high as about 2.0 on a smooth acrylic plate. Accordingly, the elastomers according to the present invention apparently show a high frictional force with the contacting surface of shorts or the like when the article is worn.

The load changes of the material 1 according to the present invention and the comparative material 1 in translational motion are shown in FIGS. 4 and 5, respectively.

It will be understood from FIG. 4 that the article of the present invention repeats contacting with the contacting surface-peeling in translational motion. In other words, the article of the present invention moves like a measuring worm so that slippage can be effectively prevented due to the stiff movement as mentioned above.

TABLE 1

| Properties | Sample 1 according to the present invention | Sample 2 according to the present invention | Sample 3 according to the present invention |
|---|---|---|---|
| resin component | 1,2-polybutadiene (Kalsoft cc10A, manufactured by Takiron Co., Ltd.) | 1,2-polybutadiene (RB-830 manufactured by Japan Synthetic Rubber Co., Ltd.) | ethylene-ethyl acrylate copolymer (DPDJ-6182 manufactured by Nippon Unicar Company Limited) |
| molded form | foamed sheet | film | film |
| thickness | 1 mm | 50μ | 50μ |
| breaking strength (kg/cm$^2$) | 10.3 (JIS K6767) | 245 (JIS Z1702) | 120 (JIS Z1702) |
| breaking elongation (%) | 360 (JIS K6767) | 510 (JIS Z1702) | 800 (JIS Z1702) |
| 50% elongation stress (kg/cm$^2$) | 0.575 | 21.8 | 47.5 |

Example 3

The slippage preventing ability by which the effect of the present invention can be confirmed was evaluated according to the following procedure.

A test piece 14 was set on a movable female waist model 12 as shown in FIG. 6 in such a way as shown in FIG. 7. Shorts were put on the model, which was then moved in a fashion simulating walking at a rate of 50 m/min for 10 minutes. A distance of slippage between the position where the test piece had been set on and the position of the test piece after the movement was measured. It was defined as the slippage preventing ability in a dry state.

5 g of an artificial blood was absorbed in a test piece in a worn state through a dropping tube 13. Thereafter, movement in a walking fashion was made at the same rate for 10 minutes. The resulting slippage was measured in the same manner as described above, and was defined as the slippage preventing ability in an absorption state.

Two kinds of test pieces, namely a constitution A (FIG. 1($a$)) and a constitution B (FIG. 1($b$)), were used. In one of the consititutions, 2.0 g of fluff pulp, 1.2 g of an absorbent tissue and 0.3 g of a superabsorbent polymer were used in the absorbent layer. A nonwoven fabric of polyolefin having a weight of 20 g/m$^2$, comprising conjugate fibers of polyethylene and polypropylene and polyester at a weight ratio thereof of 30 to 70, was used for the surface material.

A foamed urethane and a low-density polyethylene was used as controls for the same measurement as described above.

The results are shown in Table 3.

It will be apparent from Table 3 that slippage can be effectively prevented against movement in a worn state in the article of the present invention.

TABLE 3

| No. | Constitution of napkin | Test piece Material | Thickness | Slippage (mm) in dry state | Slippage (mm) in absorption state |
|---|---|---|---|---|---|
| Article according to the present invention | | | | | |
| 1 | A | Sample 1 according to the present invention (foamed polybutadiene) | 1.0 mm | 1 | 2 |
| 2 | A | Sample 1 according to the present invention (foamed polybutadiene) | 1.5 mm | 1 | 1 |
| 3 | B | Sample 1 according to the present invention (foamed polybutadiene) | 1.0 mm | 1 | 1 |
| 4 | B | Sample 1 according to the present invention (foamed polybutadiene) | 1.5 mm | ~0 | ~0 |
| 5 | A | Sample 2 according to the present invention (polybutadiene) | 50μ | 4 | 4 |
| 6 | B | Sample 2 according to the present invention (polybutadiene) | 50μ | 3 | 3 |
| 7 | A | Sample 3 according to the present invention (ethylene-ethyl acrylate copolymer) | 50μ | 3 | 4 |
| 8 | B | Sample 3 according to the present invention (ethylene-ethyl acrylate copolymer) | 50μ | 2 | 3 |
| Comparative article | | | | | |
| 9 | A | Comparative sample 1 (foamed urethane) | 1.0 mm | 14 | 11 |
| 10 | A | Comparative sample 2 (polyethylene) | 50μ | 12 | 10 |

What is claimed is:

1. An absorbent article comprising,
   a surface sheet,
   a back sheet, and
   an absorbent layer disposed therebetween wherein a part or all of said back sheet is not in contact with the skin of a user,
   said back sheet having
   (a) a coefficient of kinetic friction against an acrylic resin plate of 1.5 or higher,
   (b) an elasticity such that said back sheet breaks at a length of 300 percent or greater, based on the original length, and
   (c) a force of 100 kg/cm$^2$ or less being required to stretch said back sheet by 50 percent based on the original length.

2. An absorbent article as claimed in claim 1, in which a part or all of said back sheet is an elastomer selected from the group consisting of a conjugated diene polymer, polyethylene, polypropylene, polybutylene and polyvinylidene chloride.

3. An absorbent article as claimed in claim 1, in which a part or all of said back sheet is formed from an elastomer.

4. An absorbent article according to claim 1 wherein said backing sheet extends along the sides of said absorbent layer and covers a portion of said surface sheet.

5. An absorbent article according to claim 1 wherein said surface sheet extends along the lateral sides of said absorbent layer and attaches to said back sheet at the base of said absorbent layer.

6. An absorbent article according to claim 1 wherein said surface sheet and said back sheet meet at the mid-lateral sides of said absorbent layer.

* * * * *